(12) United States Patent
Dietz et al.

(10) Patent No.: US 11,723,824 B2
(45) Date of Patent: Aug. 15, 2023

(54) BASE MODULE, MEDICAL SYSTEM AND METHOD FOR OPERATION OF THE MEDICAL SYSTEM

(71) Applicant: Siemens Healthcare GmbH, Erlangen (DE)

(72) Inventors: Volker Dietz, Hoechstadt an der Aisch (DE); Elmar Garcia, Erlangen (DE); Franz Dirauf, Bad Staffelstein (DE); Josef Deuringer, Herzogenaurach (DE)

(73) Assignee: Siemens Healthcare GMBH, Erlangen (DE)

( * ) Notice: Subject to any disclaimer, the term of this patent is extended or adjusted under 35 U.S.C. 154(b) by 318 days.

(21) Appl. No.: 17/113,323

(22) Filed: Dec. 7, 2020

(65) Prior Publication Data
US 2021/0177683 A1 Jun. 17, 2021

(30) Foreign Application Priority Data
Dec. 17, 2019 (EP) .................................... 19216765

(51) Int. Cl.
*A61G 7/08* (2006.01)
*B60B 33/00* (2006.01)
*B60B 33/06* (2006.01)

(52) U.S. Cl.
CPC ............ *A61G 7/08* (2013.01); *B60B 33/0044* (2013.01); *B60B 33/06* (2013.01);
(Continued)

(58) Field of Classification Search
CPC .. A61G 7/08; A61G 2203/18; A61G 2203/30; B60B 33/0044; B60B 33/06; A61B 6/4405; G16H 40/67; H04L 67/12
See application file for complete search history.

(56) References Cited

U.S. PATENT DOCUMENTS 3,876,255 A 4/1975 Ilon
4,605,086 A 8/1986 Marom
(Continued)

FOREIGN PATENT DOCUMENTS

DE 102014208463 A1 11/2015
DE 102014115901 A1 5/2016
(Continued)

OTHER PUBLICATIONS https://www.krausse-gmbh.de/industriestossdaempfer/produkte/kme-daempfer-m6-m36.html.
European Search Report, dated Jun. 6, 2020.

*Primary Examiner* — Fredrick C Conley
(74) *Attorney, Agent, or Firm* — Harness, Dickey & Pierce, P.L.C.

(57) ABSTRACT

A base module is for a mobile medical system, designed to cover distances autonomously or semi-autonomously. The base module includes a chassis having a plurality of rolling bodies. The rolling bodies are mounted to rotate about axes of rotation and, via adjusting devices, are adjustable in the vertical direction such that each respective rolling body is movable between a first position, in which the respective rolling body is in contact with a floor area, and a second position, in which the respective rolling body is spaced apart from the floor area. A medical system includes a base module of an embodiment. A method for operation of the medical system is also disclosed.

26 Claims, 4 Drawing Sheets

(52) U.S. Cl.
CPC ...... *A61G 2203/18* (2013.01); *A61G 2203/30* (2013.01); *A61G 2210/50* (2013.01)

(56) References Cited

U.S. PATENT DOCUMENTS

| | | | |
|---|---|---|---|
| 2008/0123818 A1 | 5/2008 | Alder et al. | |
| 2013/0083894 A1 | 4/2013 | Niebler et al. | |
| 2014/0094997 A1* | 4/2014 | Hyde ................ | G05D 1/0246 348/148 |
| 2015/0216487 A1* | 8/2015 | Dotzel .................. | A61B 8/40 600/407 |
| 2015/0216746 A1* | 8/2015 | Dirauf .................. | B62D 15/00 701/25 |
| 2015/0320369 A1 | 11/2015 | Jäger et al. | |
| 2017/0196748 A1* | 7/2017 | Gaiser .................. | A61G 13/08 |
| 2017/0325763 A1 | 11/2017 | Hoernig et al. | |
| 2018/0042097 A1 | 2/2018 | Kim | |
| 2018/0242932 A1 | 8/2018 | Sullivan et al. | |
| 2020/0016927 A1 | 1/2020 | Dietrich et al. | |
| 2021/0219927 A1 | 7/2021 | Dencovski et al. | |

FOREIGN PATENT DOCUMENTS

| | | |
|---|---|---|
| DE | 102016208123 A1 | 9/2017 |
| DE | 102011083876 B4 | 12/2018 |
| DE | 202019102172 U1 | 4/2019 |
| DE | 102018211669 A1 | 8/2019 |
| DE | 102019209543 A1 | 9/2020 |
| EP | 3280025 B1 | 9/2018 |
| EP | 3851050 A1 | 7/2021 |

\* cited by examiner

US 11,723,824 B2

BASE MODULE, MEDICAL SYSTEM AND METHOD FOR OPERATION OF THE MEDICAL SYSTEM

PRIORITY STATEMENT

The present application hereby claims priority under 35 U.S.C. § 119 to European patent application number EP19216765.8 filed Dec. 17, 2019, the entire contents of which are hereby incorporated herein by reference.

FIELD

Example embodiments of the application generally relate to a base module for a mobile medical system, which is designed for autonomous and/or semi-autonomous movement; the medical system designed for the autonomous or semi-autonomous covering of distances; and to a method for operation of a mobile medical system of this kind. The medical system is a general kind of platform, which is used, in particular, as a base for the transportation of imaging devices, medical equipment and/or loads, in particular in a clinical environment.

BACKGROUND

The megatrend for electrification, automation and digitization is not only pervading the field of industry (Key word: Industry 4.0) but is also reflected in the development of medical processes, clinical methods and medical equipment, in particular of imaging devices. This development is generally referred to using the catchwords Digital Hospital or Hospital 2.0.

Mobile medical systems, for example mobile imaging systems, which are designed to cover routes or distances, for example within a hospital, autonomously or semi-autonomously are known in the field of medical technology. Thus an autonomously or a semi-autonomously movable or mobile imaging system is known, for example, from US 2018/0242932 A1.

In addition to mobile medical systems of this kind, inter alia measures are proposed which relate, for example, to the optimization and digitization of existing control processes for such medical systems. DE 10 2014 208 463 A1, for example, thus describes a mobile medical system designed as a mobile patient couch, and a method for controlling such a patient couch.

The majority of medical systems installed in hospitals, medical centers and doctor's surgeries are currently not yet actually designed to cover distances autonomously or semi-autonomously. Even robot-assisted medical systems are largely permanently installed, it being possible for them to provide a high level of degrees of freedom of the controlled movement despite the permanent installation. DE 10 2011 083 876 B4 discloses, for example, a stationary imaging system, which comprises a highly mobile X-ray system.

DE 10 2014 115 901 A1 describes a floor platform for operating tables, which comprises an interface for fastening of a patient support unit for supporting a patient, and an omnidirectional, electrical drive unit. The drive unit is designed in such a way that the floor platform can be moved and rotated in any desired direction within a predetermined plane solely by the drive unit. Furthermore, an operating unit is provided for controlling the drive unit, wherein this comprises a manual actuating element. The operating unit has, moreover, a control unit, which determines actuation signals for the drive unit as a function of actuation of the actuating element and transfers them to the drive unit. The drive unit moves the floor platform on the basis of the actuation signals. The drive unit of the described medical system comprises a plurality of driven wheels, which can be actuated independently of each other, wherein the control unit controls the direction of movement of the floor platform by way of individual actuation of the driven wheels.

The medical system in DE 10 2014 115 901 A1 is very laborious and expensive to implement since it has eight complex Mecanum wheels. An omniwheel (also: omnidirectional wheel) is referred to as a Mecanum wheel here, in which the running surface of the main wheel is formed by rollers whose axes are obliquely arranged in respect of the tangential direction of the main wheel. Since a plurality of Mecanum wheels are used, the medical system is susceptible to faults and, as a rule, an increased maintenance requirement should be assumed. The medical system is not universally usable either but can only be designed for fastening of a patient support unit.

A mobile medical system is known from US 2018/0242932 A1, which has two different drive mechanisms. Firstly, what is known as a fine movement mechanism is provided, which comprises, for example, a plurality of driven wheels. Secondly, what is known as a gross movement mechanism is provided, which comprises a plurality of likewise omnidirectional wheel assemblies whose design substantially matches that of the Mecanum wheels. What is known as a belt drive is proposed as an alternative type of drive to the plurality of driven wheels. Use of drive systems with two different designs in a mobile medical system is laborious, expensive and, as a rule, susceptible to faults and entails an increased maintenance requirement, therefore. The proposed medical system is not universally usable either but provided only for a mobile imaging device.

SUMMARY

The inventors have discovered that commercially available medical imaging devices or imaging modalities or patient couches are generally not designed for autonomous or semi-autonomous movement, and instead have to be brought manually by the user to the respective point of use. While the person is moving the mobile device by hand, the member of staff is tied, in particular this person cannot undertake any further tasks, in particular medically relevant ones.

Embodiments of the present invention disclose an improved medical system, which is designed to autonomously or semi-autonomously cover distances. It is a particular, at least one embodiment of the present invention discloses a base module with a chassis for a medical system and an improved method for operation of a medical system.

Embodiments are directed to a base module, a medical system and a method for operation of the medical system. Advantageous embodiments of the invention are the subject matter of the claims.

At least one embodiment is directed to a base module for a mobile medical system, designed to cover distances autonomously or semi-autonomously, comprising:
a chassis including
a plurality of rolling bodies, mounted to rotate about respective axes of rotation, and
adjusting devices, configured to rotate respective rolling bodies of the plurality of rolling bodies, the adjusting devices being adjustable in a vertical direction such that each respective rolling body, of the plurality of rolling bodies, is movable between a first position, in which the respective rolling body is in contact with a floor area, and a second position, in which the respective rolling body is spaced apart from the floor area.

At least one embodiment of the invention also relates to a medical system. The medical system is designed to cover distances autonomously or semi-autonomously and comprises:

the base module of an embodiment, an environment detecting module, which has an environment sensor system designed for detecting the environment of the medical system and a control module for controlling the movement of the base module by taking into account the environment of the medical system detected by sensors by way of the environment detecting module.

At least one embodiment of the invention also relates to a method for operating a medical system of an embodiment, wherein the control module, for controlling movement, generates movement control commands and for execution, transmits them to the base module, wherein the execution of at least one of the movement control commands by the base module includes the adjustment of at least one of the rolling bodies in the vertical direction.

At least one embodiment of the invention also relates to a method for operating a medical system including a medical system of including a base module including a chassis including a plurality of rolling bodies, mounted to rotate about respective axes of rotation, and adjusting devices;

an environment detecting module, including environment sensors for detecting an environment of the medical system; and a control module for controlling movement of the base module, taking into account the environment of the medical system detected by the environment sensors of the environment detecting module, wherein the control module includes a user interface and is designed for at least one of voice control and gesture control, the method comprising:

generating, via the control module, movement control commands; and transmitting the movement control commands to the base module for execution of the movement control commands, wherein the execution of at least one of the movement control commands by the base module includes adjusting at least one of the plurality of rolling bodies in the vertical direction.

BRIEF DESCRIPTION OF THE DRAWINGS

Reference is made for a further description of the invention to the example embodiment shown in the figures. In the drawings in a schematic representation.

Identical or mutually corresponding parts or components are provided with the same reference numerals in all figures.

DETAILED DESCRIPTION OF THE EXAMPLE EMBODIMENTS

Figure 1:
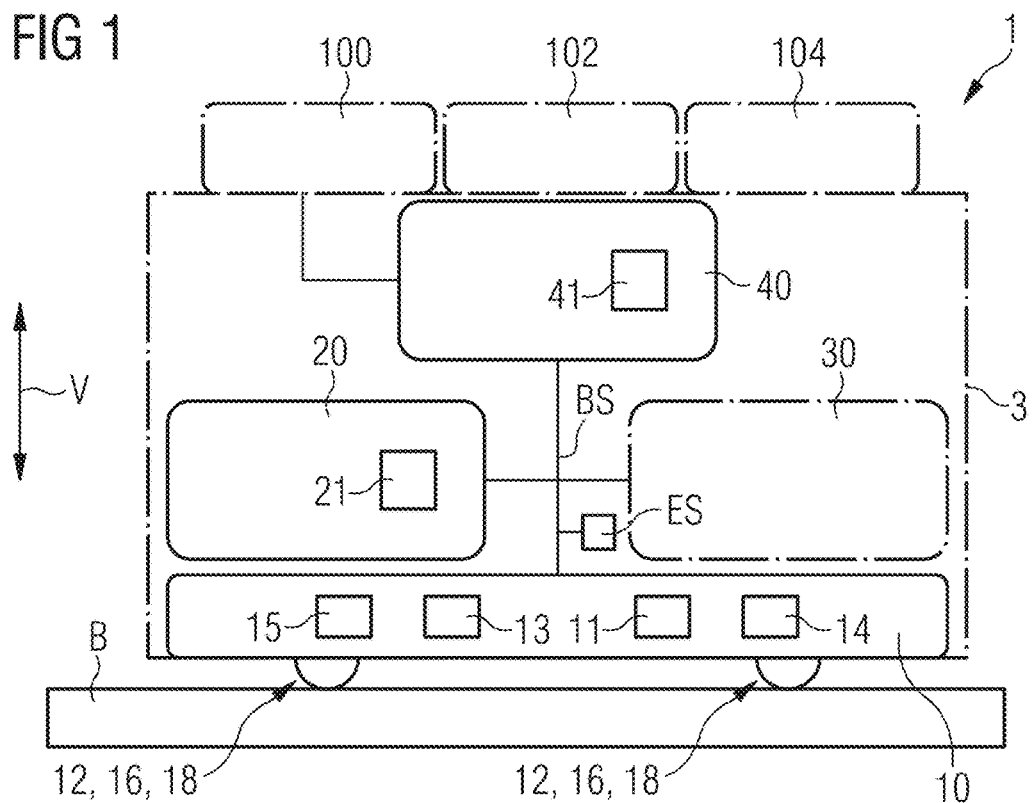
FIG. 1: shows the modular construction of a mobile medical system, which is designed for autonomous or semi-autonomous covering of distances.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A base module for a mobile medical system, which is designed to cover distances autonomously or semi-autonomously, comprises a chassis having a plurality of rolling bodies. The rolling bodies are mounted so as to rotate about axes of rotation and can be adjusted in the vertical direction by way of adjusting devices in such a way that each of the rolling bodies can be moved between a first position, in which the respective rolling body is in contact with a floor area, and a second position, in which the respective rolling body is spaced apart from the floor area.

At least one embodiment of the present invention provides an alternative, relatively simply constructed and modular system solution for an autonomously or semi-autonomously movable or mobile medical system. The above-mentioned base module is used to move the modular medical system. The adaptability of the rolling bodies in the vertical direction means that various maneuvers can be easily performed, in particular in a small space. Rolling bodies, which would hinder or impair the execution of the respective maneuvers, are automatically retracted accordingly, so that they have no further contact with the floor area. In this way mechanically complex components, such as omnidirectional wheels or Mecanum wheels, can be omitted.

At least one embodiment of the inventive medical system can be used, for example, as a mobile platform for imaging devices, such as C-arm X-ray equipment, computed tomography units, ultrasound devices, and/or for medical equipment, patient couches or the like. In possible embodiments, the medical system can represent a cost-efficient variant of a mobile platform for medicine containers or the like, which are equipped modularly and according to requirements, in other words, according to instantaneous use. The medical system can be used in a wide range of applications, therefore.

The medical system is predominantly provided for use in a clinical environment (hospital, medical center, doctor's surgery, etc.) and within the meaning of the modular design principle can be used for a wide range of applications, for example for imaging devices, such as C-arms, computed tomography units or ultrasound devices, and/or for medical equipment, patient couches or the like. In other embodiments, the medical system is used, for example, as a mobile trolley. To summarize, the medical system represents a mobile or movable, or rather, in respect of its location, displaceable platform to move arrangements with relatively high mass (in particular imaging modalities, but also other types of heavy mobile clinical tables, cabinets or storage containers) autonomously or at least semi-autonomously between at least two locations.

In embodiments, at least two axes of rotation of the rolling bodies are arranged relative to each other in an arrangement, which differs from a parallel or antiparallel arrangement. In other words, the chassis of the base module has rolling bodies with at least two different axes of rotation, which are oriented relative to each other at an angle, which is different from zero.

In embodiments, at least two axes of rotation of the rolling bodies are arranged relative to each other at an obtuse, in particular right, angle. The chassis of the base module has, in particular, rolling bodies with different orientations, which are used, for example, for the forwards or backwards movement of the medical system and a lateral movement of the medical system.

In embodiments, the axes of rotation of the rolling bodies of the chassis form at least an encircling, in particular rectangular or square, arrangement. Arrangements of this kind are mechanically very stable.

In embodiments, the rolling bodies are mounted to rotate in pairs respectively about the axes of rotation. In other words, at least two rolling bodies are concentrically arranged around each axis of rotation to improve the stability of the chassis. In this way adequate stability is also ensured when, for example, a rolling body has to be retracted in order to execute a particular maneuver and therefore has no further contact with the floor.

In embodiments, the adjusting device is designed as an adjustable shock absorber, in particular gas shock absorber.

In embodiments, the rolling bodies are substantially cylindrical in design. The rolling bodies have, for example, a substantially constant diameter. As an alternative, in embodiments, the rolling bodies have a camber, in particular in such a way that the diameter of the rolling body tapers at the end.

In embodiments, the base module has a vibration sensor system for detecting vibrations, in particular vibrations occurring during movement. The vibration sensor system has, for example, suitably designed acceleration sensors for detecting the vibrations.

In embodiments, the base module has an acceleration sensor system for detecting accelerations, in particular collisions. The acceleration sensor system has, for example, suitably designed acceleration sensors, in particular for detecting collisions with moving or stationary objects.

At least one embodiment of the invention also relates to a medical system. The medical system is designed to cover distances autonomously or semi-autonomously and comprises the base module of an embodiment,
an environment detecting module, which has an environment sensor system designed for detecting the environment of the medical system and
a control module for controlling the movement of the base module by taking into account the environment of the medical system detected by sensors by way of the environment detecting module.

The autonomous or at least semi-autonomous movement is executed in that the medical system represents a support platform for a plurality of modules which can be interconnected. In embodiments, the medical system comprises a drive module, which is implemented by the above-described base module. The base module is used at least predominantly for the purely mechanical movement of the medical system and comprises a relatively simple and robust mechanism, which enables a movement of the medical system on simply constructed rolling bodies.

The medical system also has the environment detecting module, which, in embodiments, comprises a plurality of sensor elements/sensing devices and for example further, varied sensor elements (for example video/camera, LIDAR, near-field radar, wide-field radar, etc.) and are designed for detecting the environment of the medical system.

The medical system also has the control module, which is provided to internally process and/or qualify information from the environment detecting module. The control module generates, for example as a function of this information, movement control commands, which it forwards to the base module for controlling the movement of the medical system.

To obtain autonomy or autarchy of electrical supply networks that are possibly present, in embodiments, the medical system optionally comprises an energy storage module, which provides the current and voltage supply for the modules already mentioned.

The base module, the environment detecting module, the possibly optionally provided energy storage module and the control module will be referred to below in summary as modules of the medical system. In embodiments, these modules are designed to be intercommunication- and network-capable. For this, the modules are provided, for example, with suitable interfaces, which are designed for wireless or wired communication, in particular in real time. The interfaces comprise, for example, an internal bus system, which is implemented in particular by an Ethernet, a CAN bus or by a different field bus system suitable for medical applications. In embodiments, the Ethernet, the CAN bus and/or the field bus system have real-time capability, so that the modules can enter into real-time communication with each other. In embodiments, the modules have one or more microchip(s), processor(s), controller(s) and/or other electronic components, which are designed for carrying out digital operations. In embodiments, the modules also have memories, in particular non-volatile memories, and working memories, in particular volatile working memories. In embodiments, operating systems (OS) and/or further software packages, in particular in the respective non-volatile memories, are installed on all modules 10, 20, 30, 40. In embodiments, the modules are capable of on-board diagnosis and adapted, for example, to file statuses about their functionality and, in particular in the framework of a remote diagnosis/remote maintenance, transmit them to an evaluation unit or base station of an external network. The external network is, for example, a wired network or a wireless network or has both wired subnetworks as well as wireless subnetworks. The internal network or bus system has, for example, an access port to a Cloud application, adapted for remote diagnosis and/or remote maintenance.

In embodiments, the medical system is supplied with energy by way of the energy storage module already mentioned above. The control module is preferably designed to control the movement of the base module by taking into account the state-of-energy or state-of-charge of the energy storage module.

In embodiments, the control module has a user interface and is designed for voice control and/or gesture control. The user interface preferably has appropriately configured detection devices, such as microphones, optical sensors and/or cameras. Voice recognition software and/or gesture recognition software is preferably implemented in the control module.

In embodiments, the medical system is designed to support and move an imaging device, medical equipment, a patient couch and/or other loads. Components of this kind can be detachably fastened or permanently installed, for example on a support platform of the medical system.

In a method for operation of the above-described medical system, the control module, for controlling the movement, generates movement control commands and transmits them for execution to the base module. The execution of at least one of the movement control commands by the base module includes the adjustment of at least one of the rolling bodies in the vertical direction. In this way rolling bodies, which would impair execution of the corresponding maneuver, can be adjusted in the vertical direction such that they have no further contact with the floor area on which the medical system moves. The respective rolling bodies are adjusted in the vertical direction as a function of the maneuver to be executed, preferably automatically.

In embodiments, movement control commands are generated as a function of data from a vibration sensor system, which is indicative, in particular, of vibrations occurring during movement. The data of the vibration sensor system is an indicator of shocks and vibrations, therefore and/or contains information about vibrations occurring during movement. This allows, in particular, conclusions to be drawn about the nature of the floor area on which the medical system moves.

In embodiments, the movement control commands are generated as a function of data of an acceleration sensor system, which is indicative, in particular, of accelerations occurring during movement. The data of the acceleration sensor system is, for example, an indicator for collisions that have possibly occurred with moving or stationary objects and can be used, in particular, to implement an automatic emergency stop of the medical system.

In embodiments, the movement control commands are generated as a function of qualified environment data, which is indicative, in particular, of the environment of the medical system. The qualified environment data is, for example, an indicator of objects present in the mediate and/or immediate environment of the medical system. Consideration of the qualified environment data is critical to path planning and allows, in particular, autonomous or semi-autonomous planning and covering of distances, in particular within a clinical environment or a field environment.

In embodiments, the movement control commands are generated as a function of diagnostic protocols of a battery management system, which are indicative, in particular, for a state-of-charge and/or a state-of-health of an energy store. Diagnostic protocols of this kind can be used, in particular, to assess the usability of the medical system in advance.

FIG. 1 schematically shows a mobile medical system 1 designed for autonomous or at least semi-autonomous covering of distances in a schematic representation. The medical system 1 is modular and comprises a support platform 3, shown in broken lines in FIG. 1, for a plurality of network- and communication-enabled modules 10, 20, 30, 40, which are designed for the reciprocal exchange of data with appropriately wired or wireless interfaces.

The support platform 3 constitutes the basis of a modular concept in which, for example in an interior region of the support platform 3, a plurality of different modules 10, 20, 30, 40 are arranged and interconnected, so that they can functionally communicate with each other. FIG. 1 shows only one example embodiment of this modular concept, which should be understood as non-limiting, in other words, number and type of modules 10, 20, 30, 40, with which the support platform 3 is equipped is generally adjusted "on demand", in other words, as needed according to the desired field of application.

The modules 10, 20, 30, 40 are, in particular, a base module 10, an environment detecting module 20, a possibly optionally provided energy storage module 30 and a control module 40.

Close to the floor is the base module 10 with a chassis 12 and a drive 14, for example an electrical one. The chassis 12 comprises a plurality of motor-driven or drivable drive devices 16, which are designed substantially as cylindrical or barrel-shaped rolling bodies 18. As shown in particular in FIG. 3, in advantageous embodiments, the diameter of the rolling bodies 18 is not constant but has a camber such that the diameter decreases at least slightly in the direction of the axial ends of the respective rolling body 18.

The rolling bodies 18 are provided, for example, with a rubber, linoleum, or plastics material surface. Linoleum is advantageously anti-static, slightly fungicidal and bacteriostatic, in other words, it inhibits possible growth of bacteria. The reason for this is the permanent emission of small quantities of various aldehydes, which originate from what is known as linseed oil autooxidation of air or from the oxidation reaction in the production process. For this reason linoleum is often used as a floor covering in buildings with stringent hygiene requirements, such as hospitals or doctor's surgeries.

In embodiments, the barrel-shaped rolling bodies 18 can have a stainless steel construction, which is designed for receiving a roller, for example made of solid rubber. In other designs, the stainless steel construction is designed such that plastics material rollers can be inserted in them. The plastics material rollers have, for example, a thermoplastic polyurethane tread. This facilitates mobility of the movability of the support platform 3 or of the medical system 1.

The drive devices 16 are arranged in a comparatively simple drive mechanism, which enables a movement on the rolling bodies 18.

In embodiments, corners and edges of the rolling bodies 18 are advantageously rounded in design. The simple geometric shaping of the substantially barrel-shaped or cylindrical rolling bodies 18 allows straightforward cleaning, in particular by way of common disinfection chemicals.

The support platform 3 is designed, for example, to support an imaging device 100 (also: imaging modality), further medical equipment 102 and/or additional medical loads 104 and/or further receptacles or containers. These components can be fastened, for example via toggle-type and/or clip quick-release fasteners, to the support platform 3.

In embodiments in which no imaging device 100 is attached to the support platform 3 of the modular medical system 1, the medical system 1 can be used, for example, for transportation of containers, in particular to transport surgical products contaminated with bodily fluids or aids. The containers can be detachably fastened, for example via toggle-type and/or clip quick-release fasteners, to the support platform 3.

The mobile medical system 1 also comprises the environment detecting module 20 for detecting the environment, in particular the stationary environment and stationary and/or moving objects in the environment of the medical system 1. The environment detecting module 20 is used, moreover, for planning the route. The optional energy storage module 30 is used for supplying the modules 10, 20, 30, 40 with energy, in particular electrical energy, and the control module 40 for controlling and/or regulating the movement by taking into account the environment of the medical system 1, detected in particular by sensors, and the state-of-energy or state-of-charge of the energy storage module 30.

The modules 10, 20, 30, 40 are intercommunications- and network-enabled. For this, the modules 10, 20, 30, 40 are provided with suitable interfaces, which are designed for wireless or wired communication, in particular in real time. These interfaces comprise, for example, an internal bus system BS, which is implemented, in particular, by an Ethernet, a CAN bus or by a different field bus system suitable for medical applications. In embodiments, the Ethernet, CAN bus and/or field bus system is real-time-capable, so that the modules 10, 20, 30, 40 can enter into real-time communication with each other.

The modules 10, 20, 30, 40 have one or more microchip(s), processor(s), controller(s) and/or other electronic component(s), which are designed for carrying out digital data operations. The modules 10, 20, 30, 40 also have memories, in particular non-volatile memories, and working memories, in particular volatile working memories. In embodiments, operating systems (OS) and/or further software packages, are installed, in particular in the respectively non-volatile memories, on all modules 10, 20, 30, 40.

Similar to the electrical system topology of a modern motor vehicle, in embodiments, the modules 10, 20, 30, 40 are designed to exchange protocols, in other words, in particular to send and/or receive them. In embodiments, the modules 10, 20, 30, 40 are configured as electronic control devices or comprise one or more electronic control device(s). The control devices are embedded, for example, in the modules 10, 20, 30, 40.

In embodiments, the modules 10, 20, 30, 40 communicate among themselves via a secure, real-time-capable bus system BS, which supports diagnostic protocols and is also adapted for wired or wireless communication with a further external network.

The modules 10, 20, 30, 40 are, for example, capable of on-board diagnosis and adapted to file statuses about their functionality (for example error codes or fault memory entries) in the respective memory or in a fault memory inside the module or in a memory area provided for filing faults, therefore.

The error codes or fault memory entries can be read out via diagnostic programs or what are known as diagnostic services, in particular by way of what is known as a Diagnostic Scan Tool. In particular, what is known as a "P-Code" Tool can be used, which is applied, for example, in the course of the On-Board Diagnosis (OBD) in the automotive industry.

The error codes or fault memory entries can be read out with the aid of an external evaluation unit, such as a laptop or notebook. The error codes or fault memory entries can be transmitted, for example in response to an external trigger, which is transferred, for instance in the course of a remote diagnosis and/or remote maintenance, to the respective module 10, 20, 30, 40, wirelessly or in a wired manner to the external evaluation unit or a base station, which is arranged in an external network. The external trigger is, for example, what is known as a diagnostic job, which is sent by the external evaluation unit, in particular by notebook or a Diagnostic Scan Tool or the like, and is executed in the internal network of the medical system 1 or the modules 10, 20, 30, 40.

The external network is designed, for example, as a wireless network. At least some of the intercommunications- and network-enabled modules 10, 20, 30, 40 are designed to communicate protocols not only over the internal network or over the internal bus system, in particular in real time, but are also designed in such a way that protocols can be sent on the external network and be received from there, therefore. For communication with the external network the modules 10, 20, 30, 40 or the internal network or bus system BS have/has at least appropriately designed wireless or wired external interfaces ES.

Communication with the external network enables loading of software and, in particular, what is known as OTA (Over-The-Air) updates of individual software packages. These software packages can function, for example, for operation of the modular medical system 1 and/or constitute parts of medical user software, in particular for operation of the imaging unit 100.

The internal network or bus system BS has, for example, at least one access port to a Cloud application, adapted for remote diagnosis and/or remote maintenance. This enables, in particular, a comparison of internal status data, for example of actual data of the modular medical system 1 or the modules 10, 20, 30, 40 "on board", with external standard data. The external standard data can be, for example, desired data, which is stored, in particular, in the external network of a hospital or similar medical facility. Remote maintenance of the medical system 1 and its components can be implemented, or at least supported in preparation, by these measures and/or in particular the imaging device 100 arranged on the support platform 3 can be made accessible for predictive maintenance. For example, status data of the imaging device 100 can be retrieved from a control center without one or more service engineer(s) having to be dispatched into the immediate vicinity of the imaging device 100, which is time-consuming and expensive. This has advantages in particular also in respect of the hygiene standards that are to be maintained in a clinical environment.

The base module 10 is critical for the mechanical movement of the medical system 1 or the support platform 3. It does not have any omnidirectional wheels, in particular Mecanum wheels. The chassis 12 of the base module 10 has a comparatively simple mechanism, which enables movement of the medical system 1 on simply constructed, rolling bodies 18.

The base module 10 has a vibration sensor system 11, which is designed to detect vibrations, which are produced during movement of the medical system 1. The vibration sensor system 11 comprises for this purpose, for example, an acceleration sensor.

The vibration sensor system 11 of the base module 10 is designed to recognize shocks which occur during movement. Using the detected vibrations, conclusions can be made about the nature of the route or the surface travelled on.

Figure 2:
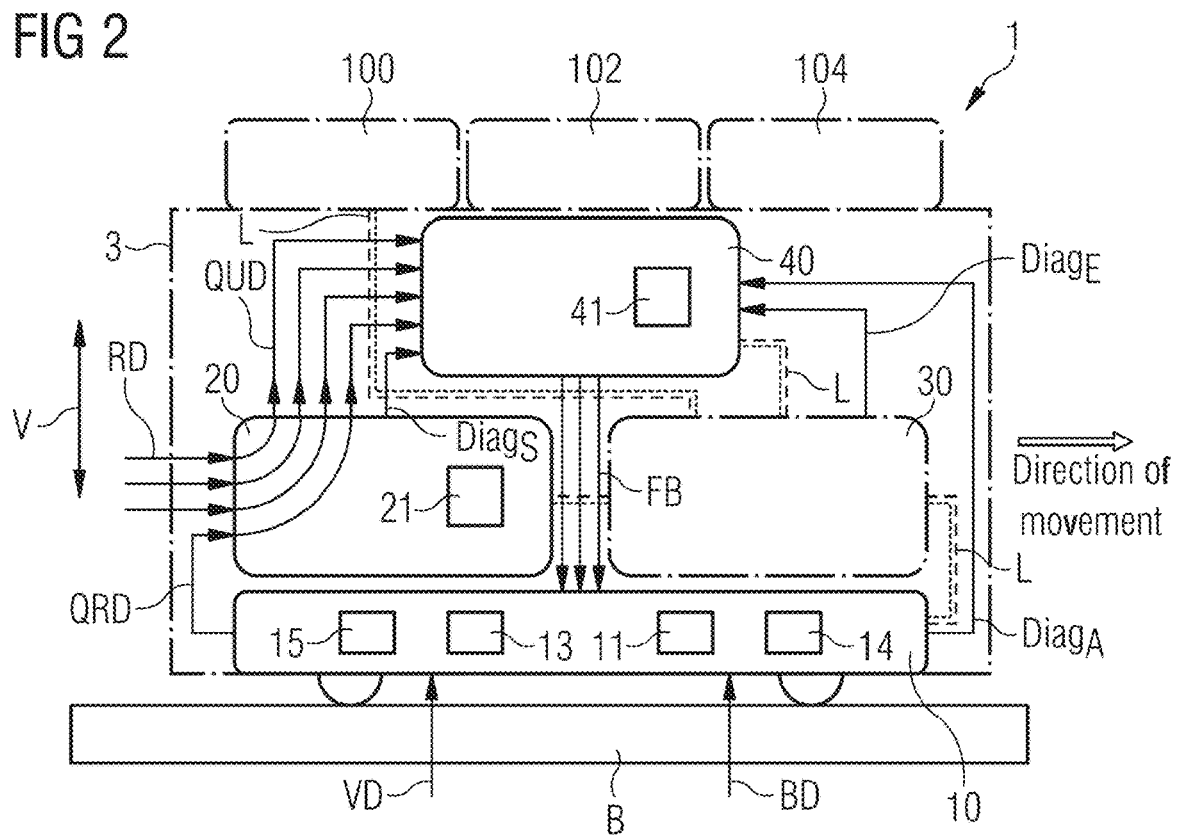
FIG. 2: shows the cooperation of the modules in a method for operation of the mobile medical system of FIG. 1.

As FIG. 2 in particular shows, in embodiments, the chassis 12 of the base module 10 is actuated on operation of the medical system 1 by the control module 40 by way of suitable movement control commands FB as a function of the detected vibrations, for example in such a way that on leaving a level surface or level floor area B, the base module 10 automatically pauses or stops the drive operation. In this way, for example, damage to the bottom of the support platform 3 and/or the base module 10 owing to uneven surface characteristics can be avoided.

The base module 10 forwards, for example, the data VD from the vibration sensor system 11 to the environment detecting module 20 by way of the bus communication. As an alternative, the data VD originating from the vibration sensor system 11 is passed directly to the control module 40 via the internal bus system BS.

Furthermore, the base module 10 has, for example, an acceleration sensor system 13, which is designed, in particular, to detect accelerations which occur on moving. In embodiments, this acceleration sensor system 13 comprises at least one acceleration sensor, which has, in particular, a different structural form to the acceleration sensor of the vibration sensor system 11.

The acceleration sensor system 13 of the base module 10 is designed, in particular, to detect if movement stops or starts abruptly. This can be used as a measure of possible collisions of the medical system 1 with other moving or stationary objects, such as people, objects, walls, or the like.

The base module 10 is designed to forward the data BD from the acceleration sensor system 13 to the environment detecting module 20 by way of the bus communication. As an alternative, the base module 10 is designed to forward the data acquired by the acceleration sensor system 13 directly internally to the control module 40 via bus communication.

In embodiments, the base module 10 has a discrete electrical diagnostic cable DiagA via which diagnostic protocols, in particular a status monitoring of the base module 10, identified collisions, recognition of a rough route or the like, can be passed to the control module 40.

In alternative embodiments, no discrete diagnostic cable is provided. In this case the diagnostic protocols are sent and received, for example, via the above-described bus communication, via the bus system BS, therefore.

FIG. 2 schematically illustrates the construction and the procedural cooperation of the modules 10, 20, 30, 40 of the medical system 1. The base module 10 of the illustrated medical system 1 has a discrete diagnostic cable DiagA. In the illustrated medical system 1, which is to be understood as merely an example, the rough route recognition by the base module 10, implemented by way of the acceleration sensor system 13 and/or the vibration sensor system 11, is transmitted as qualified raw data QRD via bus communication to the environment detecting module 20 and qualified further there.

Figure 3:
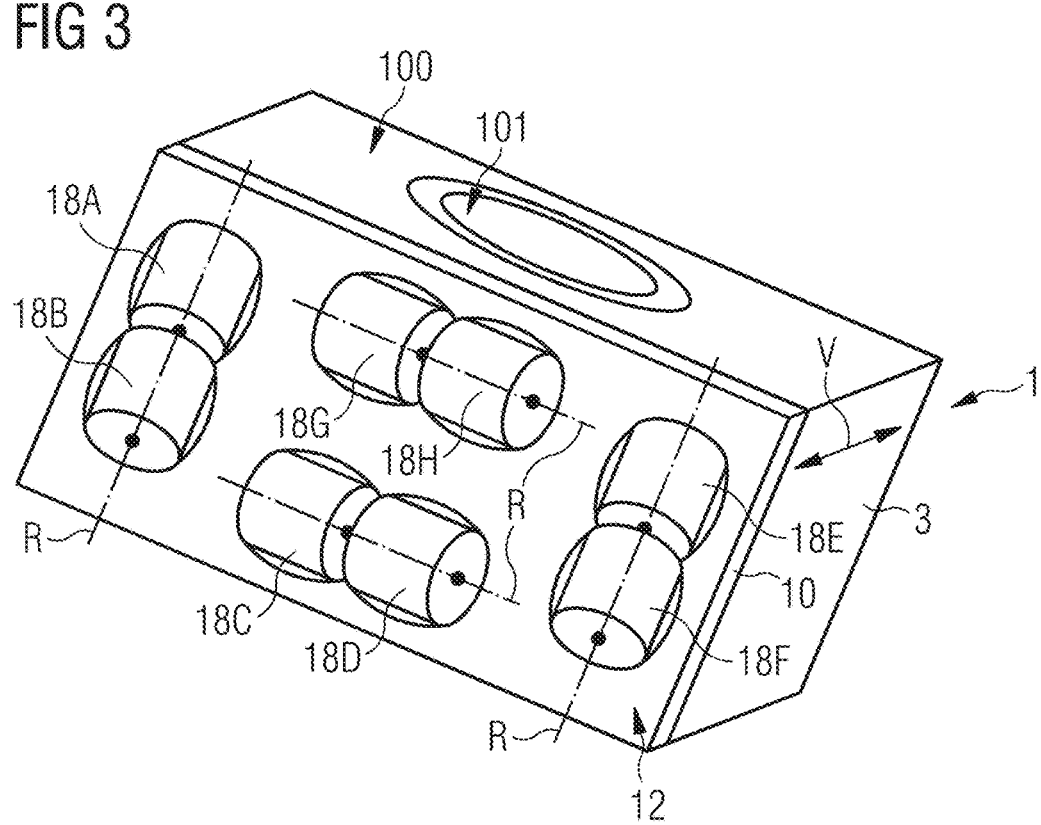
FIG. 3 shows a mobile medical system with an imaging device according to one possible example embodiment of the invention.
Figure 4:
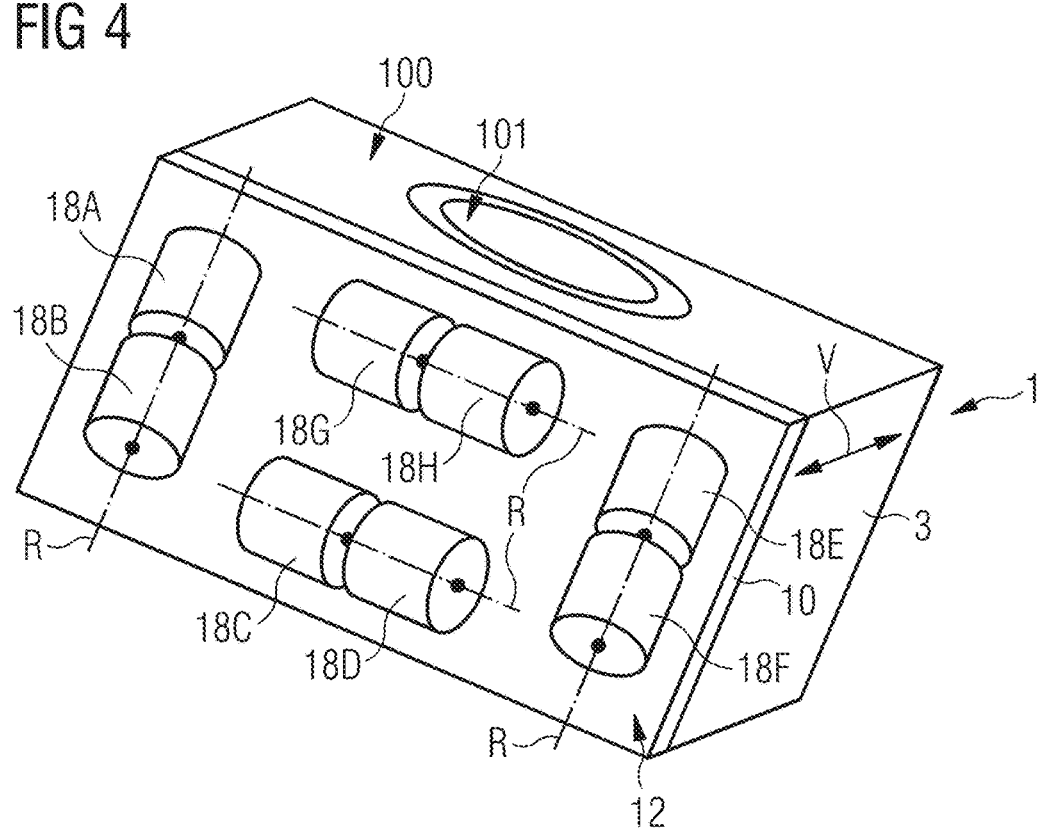
FIG. 4 shows a mobile medical system with an imaging device according to a further possible example embodiment of the invention.
Figure 5:
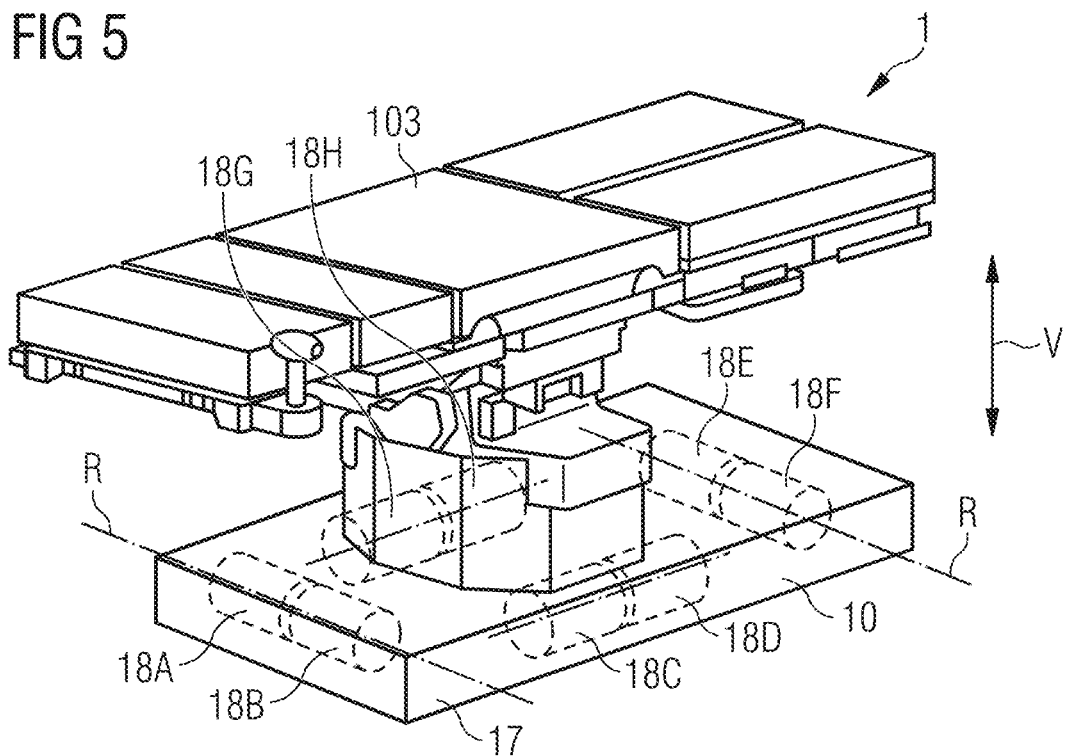
FIG. 5 shows a mobile medical system with a patient couch according to a further possible example embodiment of the invention.

As FIGS. 3, 4 and 5 in particular illustrate, the chassis 12 of the base module 10 comprises a plurality of roller- or barrel-shaped rolling bodies 18, which can be controlled and driven independently of each other, on which the mobile medical system 1 can move. The rolling bodies 18 can be driven, for example, via an electric drive 14 in such a way that the drive axis of the electric drive 14 matches the axis of rotation R of the respectively coupled rolling body 18. In this way rolling bodies 18 with direct drive are implemented in embodiments, therefore.

FIGS. 3, 4 and 5 illustrate example chassis 12, each with eight rolling bodies 18 which can be driven and controlled independently of each other.

FIGS. 3 and 4 show by way of example a medical system 1 with an imaging device 100, designed as a computed tomography unit (CT), which has a mobile gantry 101, in a perspective view. The rolling bodies 18 are arranged in pairs respectively along the axes of rotation R in such a way that when the medical system 1 moves with floor contact they rotate and roll statically stably on the floor without tilting to the side.

The illustrated rollers represent examples of the barrel-shaped rolling bodies 18. Each rolling bodies 18A, 18B, 18C, 18D, 18E, 18F, 18G, 18H can be driven and controlled individually.

Each rolling body 18A, 18B, 18C, 18D, 18E, 18F, 18G, 18H has, for example in its geometric interior, an electric drive 14 non-rotatably connected to the base module 10, and which is designed to provide a drive moment. The electric drive 14 can rotate counterclockwise as well as, with appropriate actuation, clockwise. Forwards and backwards rotation of the rolling bodies 18A, 18B, 18C, 18D, 18E, 18F, 18G, 18H can be induced as a result.

The rolling bodies 18A, 18B, 18C, 18D, 18E, 18F, 18G, 18H are oriented in pairs respectively along one axis of rotation R respectively, so that four different axes of rotation R are formed. The axes of rotation R are arranged, for example, at a right angle to each other, in particular in a rectangle or in a square, with the axes of rotation R running, for example, in each case parallel to side faces of the base module 10 or the support platform 3. The chassis 12 accordingly comprises four axles for a movement of the medical system 1 forwards, backwards, to the right and to the left.

The rolling bodies 18, 18A, 18B, 18C, 18D, 18E, 18F, 18G, 18H do not have, in particular in the embodiment shown in FIG. 3, constant diameters, but have a cambered design, so that in each case only one point of contact with the floor area B is formed, which is located, for example centrally, on the respective rolling bodies 18, 18A, 18B, 18C, 18D, 18E, 18F, 18G, 18H. In roller or bearing technology a camber is a purposeful barrel-like, for example central, thickened portion of a roller or rolling body. In particular, instead of points of contact, cylindrical, non-cambered rolling bodies 18 form contact lines with the floor area B on which the medical system 1 moves. This results in increased rolling friction. Cambered rolling bodies 18, 18A, 18B, 18C, 18D, 18E, 18F, 18G, 18H have lower rolling friction and entail improved static determination in respect of the structural stability of the base module 10.

FIG. 4 shows by way of example an embodiment with cylindrical rolling bodies 18, 18A, 18B, 18C, 18D, 18E, 18F, 18G, 18H without camber.

FIG. 5 shows an example embodiment of the mobile medical system 1, which supports as medical equipment 102 a patient couch 103. The base module 10 with the rolling bodies 18, 18A, 18B, 18C, 18D, 18E, 18F, 18G, 18H, which can be controlled and driven independently of each other, substantially corresponds to the design already described with reference to FIGS. 3 and 4. The base module 10 has an encircling hygiene apron 17 in the region close to the floor.

The drive concept mentioned above with eight rolling bodies 18, 18A, 18B, 18C, 18D, 18E, 18F, 18G, 18H, which can be controlled and driven independently of each other, is equally capable of moving an imaging device 100, in particular a mobile C-arm or a computed tomography unit with gantry 101, or a patient couch 103, therefore.

The medical system 1 can be moved as follows: if, for example the rolling bodies 18A, 18B and/or the rolling bodies 18E, 18F (cf. in particular FIGS. 3 and 4) are set in rotation, the base module 10 travels in a direction, forwards or backwards depending on the actuation of the electric drives 14, which are located, for example, inside the rolling bodies 18A, 18B, 18E, 18F. If, by contrast, the rolling bodies 18G, 18H and/or the rolling bodies 18C, 18D are driven (cf. in particular FIGS. 3 and 4), the base module 10 travels in a lateral direction, corresponding to the actuation of the electric drives 14. If, by contrast, only the two rollers 18B and 18E are driven (cf. in particular FIGS. 3 and 4), the base module 10 executes a left turn. If, by contrast, only the two rollers 18A and 18F are driven (cf. in particular FIGS. 3 and 4), the base module 10 executes a right turn.

It is immediately obvious, in particular from the representation in FIGS. 3 and 4, that the base module 10 with the rolling bodies 18, 18A, 18B, 18C, 18D, 18E, 18F, 18G, 18H, which can be controlled and driven independently of each other, can move particularly easily. In particular, no complex omniwheels and in particular no complex Mecanum wheels are needed for this.

In embodiments, one or more rolling bodies 18, 18A, 18B, 18C, 18D, 18E, 18F, 18G, 18H is/are driven by an electric drive 14 via a gear. An indirect drive is implemented in this way, therefore.

For the movement of the medical system 1 with the aid of rolling bodies 18, 18A, 18B, 18C, 18D, 18E, 18F, 18G, 18H, which can be driven and controlled independently of each other, it is provided that the rolling bodies 18, 18A, 18B, 18C, 18D, 18E, 18F, 18G, 18H can be retracted and extended in the vertical direction. With a movement of the base module 10 in one direction, for example with the above-described forwards movement, for example the rolling bodies 18A, 18B and/or the rolling bodies 18E, 18F are driven. In order for this maneuver to not be adversely affected by the rolling bodies 18C, 18D, 18G, 18H that are not needed, these rolling bodies 18C, 18V, 18G, 18H are retracted. The material abrasion of the rolling bodies 18C, 18D, 18G, 18H is also minimized in this way. For this, for example an adjusting device 15, in particular a mechatronic adjusting device 15, is provided which is designed to adjust the rolling bodies 18, 18A, 18B, 18C, 18D, 18E, 18F, 18G, 18H individually in the vertical direction V. The adjusting device 15 has for this purpose, for example, a frame and an actuator. The rolling bodies 18, 18A, 18B, 18C, 18D, 18E, 18F, 18G, 18H are typically resiliently mounted, so that the spring movement on retraction of the rolling bodies 18, 18A, 18B, 18C, 18D, 18E, 18F, 18G, 18H is shortened in the vertical direction V.

By adjusting the rolling bodies 18, 18A, 18B, 18C, 18D, 18E, 18F, 18G, 18H in the vertical direction V, the rolling bodies 18, 18A, 18B, 18C, 18D, 18E, 18F, 18G, 18H that are not needed during a particular maneuver can be retracted in such a way that they have no further contact with the floor, so that wear can be avoided. The adjusting device 15 is, for example, an adjustable shock absorber, which is designed as a spring movement adjuster.

The adjusting device 15 is designed, for example, for electric, hydraulic or pneumatic adjustment of the rolling bodies 18, 18A, 18B, 18C, 18D, 18E, 18F, 18G, 18H. For example, the adjusting device 15 is implemented by a variable gas shock absorber.

With the aid of the adjusting device 15, the rolling bodies 18, 18A, 18B, 18C, 18D, 18E, 18F, 18G, 18H can be moved between a first position, in which the rolling body 18, 18A, 18B, 18C, 18D, 18E, 18F, 18G, 18H has contact with the floor area B, and a second position, in which the rolling body 18, 18A, 18B, 18C, 18D, 18E, 18F, 18G, 18H is spaced apart from the floor area B in the vertical direction V.

Preferably, each of the rolling bodies 18, 18A, 18B, 18C, 18D, 18E, 18F, 18G, 18H, which can be controlled independently of each other, can be adjusted in the vertical direction by an adjusting device 15. For example, each rolling body 18, 18A, 18B, 18C, 18D, 18E, 18F, 18G, 18H can be operatively connected by a separate, adjustable shock absorber to the base module 10.

The environment detecting module 20 (also: sensor base) comprises an environment sensor system 21 with a plurality of sensor elements and/or sensing devices and/or further sensors. The environment sensor system 21 is designed for detecting the environment of the medical system 1. The environment detecting module 20 has environment sensors, which can detect the environment, which dynamically changes when moving. The environment sensors of the environment sensor system 21 can have different structural forms, and are designed, for example, as near-field radar sensors, far-field radar sensors, LIDAR (light detection and ranging) sensors or laser scanning sensor elements, preferably in combination with a video and/or camera sensor system. To achieve precise near-field recognition, for example, as an alternative or in addition, ultrasound sensors are provided, which are arranged on the environment detecting module 20 or are electrically connected at least to the environment detecting module 20.

The environment sensor system 21 of the environment detecting module 20 is capable, by way of the interplay of a plurality of such sensors and/or sensor elements, of detecting both dynamically moving and stationary people and objects as environment information or raw data. This raw data RD (cf. in particular FIG. 2) is passed internally to the environment detecting module 20 or processed further there. As described above, for example an operating system (OS) is operated inside the environment detecting module 20. The operating system allows, for example, image recognition software to run inside the environment detecting module 20. The raw data is qualified by way of this image recognition software, in other words, the actual recognition of people and objects results from the dynamic and stationary detection of objects, in particular of people and objects, in the environment of the medical system 1. The recognized people and objects can then be passed as qualified environment data QUD to the control module 40, in particular in such a way that a virtual mapping of the environment can be created in the control module 40, with the aim of providing collision-free path planning for the route and the direction of movement of the medical system 1.

Furthermore, in embodiments (cf. in particular FIG. 2) the medical system 1 has a discrete electrical diagnostic cable Diags, via which diagnostic protocols (for example error pattern recognition, collision recognition) can be transmitted to the control module 40 (also: control base).

In alternative embodiments to this, no discrete diagnostic cable is provided. The diagnostic protocols are sent and received in this case for example via the above-described bus communication, via the bus system BS, therefore.

Figure 6:
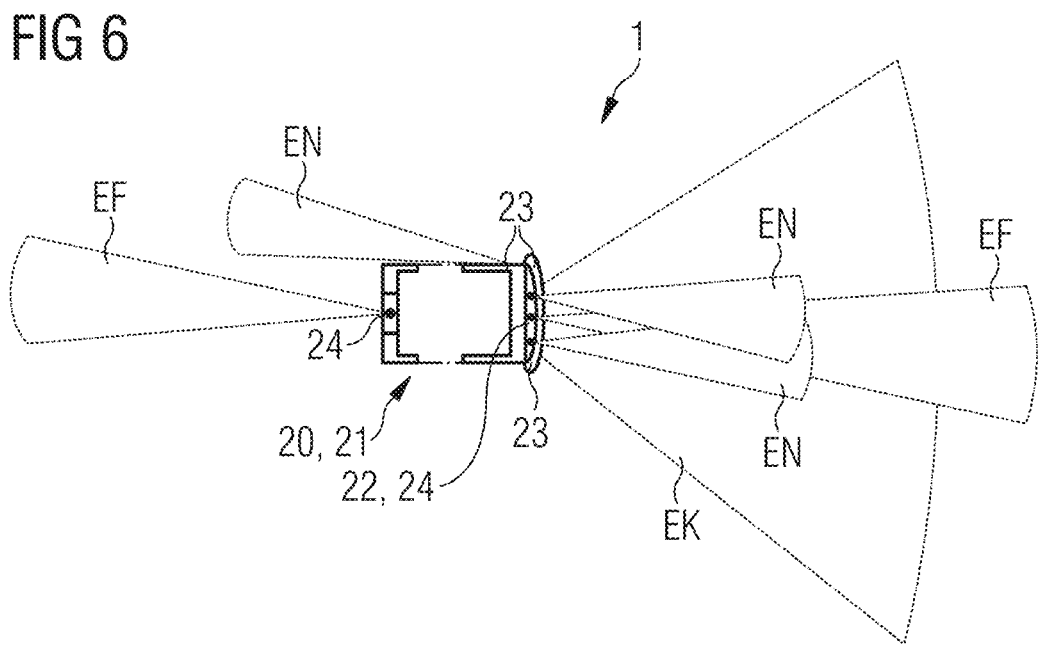
FIG. 6 shows an environment detecting module of the mobile medical system in one possible embodiment of the invention.

FIG. 6 shows one possible example embodiment of a medical system 1 with an environment detecting module 20 having an environment sensor system 21. The environment sensor system 21 comprises cameras 22, directed forwards in the direction of movement, which have a substantially conical coverage area EK. The environment sensor system 21 also comprises near-field radar sensors 23 and far-field radar sensors 24 directed forwards in the direction of movement and directed backwards opposite the direction of movement. The near-field radar sensors 23 have substantially conical coverage areas EN. The far-field radar sensors 24 accordingly have substantially conical coverage areas EF with a relatively large range. The near-field radar sensors 23 are, for example, 24 GHz radar sensors. The far-field radar sensors 24 are, for example, 77 GHz radar sensors.

Figure 7:
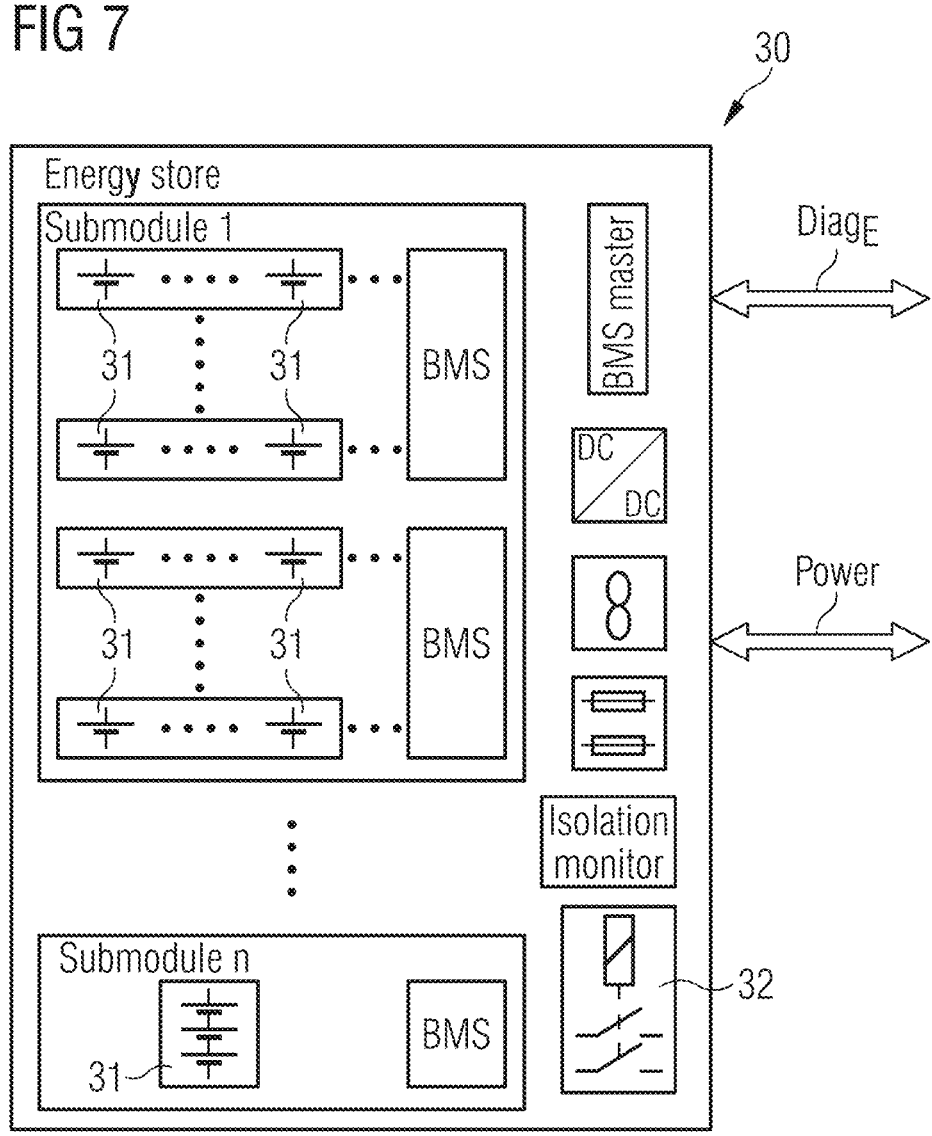
FIG. 7 shows an energy storage module of the mobile medical system in one possible embodiment of the invention.

The, in particular optionally provided, energy storage module 30 (also: supply base) is shown in one possible embodiment in FIG. 7. The energy storage module 30 is used, in particular, to ensure autonomy or autarchy of stationary supply networks.

The energy storage module 30 provides the current and voltage supply for the modules 10, 20, 30 and has for this purpose a plurality of energy cells 31 for storing electrical energy. The energy storage module 30 is connected for power supply to the modules 10, 20, 30 and the possibly optionally present imaging device 100 via electric cables L. The energy cells 31 are designed, for example, as batteries or accumulators and also have an internal control and regulating system, what is known as a battery or accumulator management system BMS. The battery management system BMS is designed, in particular, to determine the state-of-charge (SOC) and the state-of-health (SOH) of the energy cells 31, preferably in real time, so that internal and current information about a remaining life of the energy storage module 30 is always available.

The state-of-charge can be used, as shown in particular in FIG. 2, in a method for operation of the medical system 1 to transmit to the control module 40 real time information about the remaining capacity of the energy cells 31 of the energy storage module 30. The energy storage module 30 communicates with the control module 40 via a dedicated or discrete diagnostic cable DiagE or via the bus communication already described, which is provided by the bus system BS.

The state-of-health is a measure of the capability of the energy cells 31 "on board" to supply their specified power. This is important, in particular, for the assessment of the readiness of emergency power devices and an indicator of whether maintenance measures, in particular within the framework of the Predictive Maintenance are necessary.

In embodiments, the Battery Management System BMS is designed to implement a method for cell protection. This cell protection is used to meet the design limits of the energy cells 31. Operation of an energy cell 31 outside of the specified design limits generally leads to failure of the corresponding energy cell 31 and to further costs for a necessary battery change, therefore.

In embodiments, the energy storage module 30 has further communications interfaces, which facilitate access for a user or the control module 40, in particular to change control parameters of the battery management system BMS or to perform a diagnosis or test of the energy storage module 30.

Diagnostic protocols (for example state-of-charge, state-of-health, cell protection, faults that are present) during operation of the medical system 1 can be passed to the control module 40 via the discrete electric diagnostic cable DiagE. In alternative embodiments, no discrete diagnostic cable is provided. In this case the diagnostic protocols are sent and received, for example, via the bus communication described above or via the internal bus system BS.

In embodiments, the energy storage module 30 comprises, for example, energy cells 31, which are designed as nickel-metal hydride (NiMH) batteries. As an alternative, the energy cells 31 are designed, for example, as AGM batteries, lithium-ion batteries (LiB) or lithium-polymer accumulators (LiPo). For power and energy scaling the energy cells 31 are arranged, for example, in parallel and series circuits and advantageously divided into cell packages or modules and submodules.

To be able to handle as many different load scenarios as possible, in embodiments, an interconnection of different energy cells 31 is provided. This is schematically illustrated in FIG. 7 by the switch 32.

In embodiments, the energy storage module 30 comprises a fuel cell, in particular a fuel cell which can be operated with methanol, butane or the like. Preferably a controller and/or an energy management system of the fuel cell is implemented accordingly in these embodiments of the energy storage module 30. An energy storage module 30 of this kind is designed, in particular, to be used self-sufficiently energy-wise in a field environment, such as a field hospital in a war zone or disaster area. Energy self-sufficiency can provide critical advantages in respect of the availability of the medical system 1 in these cases.

In embodiments, the energy storage module 30 has, in addition to the battery management system BMS, alternatives to commercially available accumulators or batteries with a high energy density. For example, the energy storage module 30 has a lithium-air battery as the energy store. Energy stores of this kind can have a 5- to 10-times higher energy density than conventional lithium-ion batteries. In other designs the energy storage module 30 has, for example, an accumulator based on silicon, which comprises anodes made of pure silicon. Compared to current lithium-ion technology, an energy store of this kind can have, for example, an energy density that is increased tenfold. In other designs, the energy storage module 30 has, for example, what are known as lithium-iron phosphate accumulators (LiFeP accumulators) or lithium-titanate accumulators (LiTi accumulators). Since the titanate cannot react with oxides from the negative electrode, with a design of this kind the thermal runaway of the accumulator can be prevented, potentially also where mechanical damage exists. A lithium-titanate accumulator can advantageously be operated at low temperature, for example in a temperature range of −40° C. to +55° C.

In embodiments, the energy storage module 30 comprises what is known as a Redox Flow Battery (RFB), for instance in the form of a vanadium-redox accumulator, a sodium bromide-redox accumulator or a zinc-bromine accumulator, as the energy store.

In embodiments, the energy storage module 30 comprises what is known as a solid-state battery (also: solid accumulator) as the energy store. Designs of this kind have elevated reliability since with sold-state batteries of this kind both the electrodes and the electrolyte are made of solid material. In particular when compared to conventional lithium-ion accumulators, a solid-state battery of this kind has only relatively low flammability. The flammability of the energy store used can play an important part in respect of approval of the medical system 1 in a clinical environment such as a hospital, a medical center, a doctor's surgery or the like.

The control module 40 (also: control base) is designed to internally process and/or qualify data or information from the environment detecting module 20, convert it into movement control commands FB and pass it to the base module 10. The control module 40 is also responsible for the detection, processing and implementation of both user interactions and for system monitoring, calibration, interconnectivity with clinical IT systems, such as a hospital information system (HIS), a laboratory information system (LIS) or what is known as Picture Archiving and Communication system (PACS) and data security monitoring.

For detecting user interactions the control module 40 has a user interface 41, which comprises, for example, input devices, such as a touchscreen, a keyboard or a mechanism which is designed for detection and recognition of gestures of the user, and/or voice commands.

In embodiments, the control module 40 is designed, for example, to implement the following functions:

| Function | Example |
| --- | --- |
| User interactions | Motorized support of movements Voice and gesture controls |
| System monitoring | Wear predictions (Predictive Maintenance) Condition Monitoring Self-diagnosis and error displays |
| Calibration | (Semi-) autonomous in-situ calibrating routines (for example localization and navigation tasks, wear detection) |
| Data security monitoring | Data security, data integrity (for example in checksums) Data protection (for example PKI methods) |

The control module 40 comprises a powerful electronic control and regulation device to enable semi-autonomous or autonomous operation of the medical system 1 or support platform 3. In embodiments, an operating system (OS) is installed inside the control module 40, such as for example also in the remaining modules 10, 20, 30. The operating system of the control module 40 enables the installation of further software. In embodiments, path planning or navigation software is implemented inside the control module 40.

As FIG. 2 in particular illustrates, path planning or navigation takes place in a method for operation of the medical system 1 as a function of the qualified environment data QUD, in particular as a function of the people and objects detected and recognized by sensors, for example in such a way that a virtual mapping of the environment is created in the control module 40. The virtual mapping of the environment serves to provide collision-free path planning for the route and the direction of movement of the mobile medical system 1 or the support platform 3.

During operation the control module 40 transmits, for example as a function of the virtual mapping of the environment, movement control commands FB to the base module 10 for actuation of the drive devices 16. The control module 40 is designed to regulate the movement of the medical system 1 and take into account, in particular, the environment and/or the state-of-energy of the energy storage module 30 in the process, which, for example as stated above, is determined by the battery management system BMS of the energy storage module 30 and made available by way of the bus system BS to the control module 40.

Some example movement control commands FB can relate to a forwards, backwards, left turn (45 degrees), right turn (45 degrees), starboard (direction of movement to the right), port (direction of movement to the left) movement.

In embodiments, the control module 40 has what is known as a voice assistance functionality and, in particular, software designed for this purpose and a user interface 41, which is designed for detecting human speech. The user interface 41 has for this purpose, for example, microphones or the like. The voice recognition software is designed for recognizing at least one language.

By way of such voice assistance Software it is possible that people, such as doctors, hospital staff, medical-technical Assistants (MTAs), deliver voice commands, which the voice assistance Function can detect and recognize as such. The voice commands can be, for example, identical to the movement control commands FB and consist, for example, in that words such as "forwards", "left turn 45" (degrees), "right turn 45" (degrees), "backwards", "right" (starboard), "left" (port) are spoken out loud. The implementation of one of the movement control commands FB by the base module 10 includes, for example, the adjustment of at least one of the rolling bodies 18, 18A, 18B, 18C, 18D, 18E, 18F, 18G, 18H in the vertical direction V, so that the corresponding maneuver can be carried out.

During operation of the medical system 1 the voice commands or verbal commands are executed, for example, inside the control module 40 on a prioritized basis with respect to the movement control commands FB internally generated on the basis of the virtual mapping, so, as a result, in embodiments, the user (MTA, doctor, hospital staff) can control the movement of the medical system 1 completely on the basis of verbal commands, instead of having to rely on the movement control commands FB generated by the control module 40.

In the context of the description at hand here, control by way of verbal commands can be regarded as "semi-autonomous" operation of the medical system 1. Advantageously, the control module 40 has a control devices gateway, in other words, a qualified data and/or communications interface, for network communication between the internal bus system BS and an external network, for example a wireless network or a "Cloud". Over-the-air updates of individual software packages, for example, can be downloaded from the external network. In this way loading of future software updates can be advantageously offered as services.

Embodiments of the invention also relate to the advantageous technical cooperation and control methods of the modules 10, 20, 30, 40. The medical system 1 comprises the base module 10, the environment detecting module 20 and the control module 40, optionally also the energy storage module 30, to enable autonomous or at least semi-autonomous movement of the medical system 1 from one location (for example a hospital, a medical center, a doctor's surgery, a field hospital, etc.) to a further/next location, which is different from the first.

Although the invention has been illustrated and described in detail with reference to the preferred example embodiments, it is not limited hereby. A person skilled in the art can derive other variations and combinations herefrom without deviating from the fundamental idea of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical system, to cover distances autonomously or semi-autonomously, the medical system comprising:
   a base module including a chassis, the chassis including
      a plurality of rolling bodies, mounted to rotate about respective axes of rotation, and
      adjusting devices, configured to rotate respective rolling bodies of the plurality of rolling bodies, the adjusting devices being adjustable in a vertical direction such that each respective rolling body, of the plurality of rolling bodies, is movable between a first position, in which the respective rolling body is in contact with a floor area, and a second position, in which the respective rolling body is spaced apart from the floor area;
   an energy storage module configured to supply the medical system with energy; and
   a control module configured to control movement of the base module taking into account at least one of a state-of-energy or state-of-charge of the energy storage module.

2. The medical system of claim 1, wherein at least two axes of rotation of the plurality of rolling bodies are arranged relative to each other in an arrangement differing from a parallel or an antiparallel arrangement.

3. The medical system of claim 2, wherein at least two axes of rotation of the plurality of rolling bodies are arranged at an obtuse angle.

4. The medical system of claim 1, wherein at least two axes of rotation of the plurality of rolling bodies are arranged at an obtuse angle.

5. The medical system of claim 4, wherein the obtuse angle is a right angle.

6. The medical system of claim 1, wherein the respective axes of rotation of the plurality of rolling bodies form at least an encircling arrangement.

7. The medical system of claim 6, wherein the encircling arrangement is rectangular or square.

8. The medical system of claim 1, wherein the plurality of rolling bodies are mounted to rotate in pairs, respectively about the respective axes of rotation.

9. The medical system of claim 1, wherein the adjusting device is an adjustable shock absorber.

10. The medical system of claim 9, wherein the adjustable shock absorber is a gas shock absorber.

11. The medical system of claim 1, wherein the plurality of rolling bodies are substantially cylindrical in design.

12. The medical system of claim 1, wherein the plurality of rolling bodies have a camber.

13. The medical system of claim 1, further comprising:
   a vibration sensor system configured to detect vibrations.

14. The medical system of claim 13, wherein the vibration sensor system is configured to detect vibrations occurring during the movement.

15. The medical system of claim 13, further comprising:
   an acceleration sensor system configured to detect accelerations.

16. The medical system of claim 15, wherein the acceleration sensor system is configured to detect collisions.

17. The medical system of claim 1, further comprising:
   an acceleration sensor system configured to detect accelerations.

18. The medical system of claim 17, wherein the acceleration sensor system is configured to detect collisions.

19. The medical system, of claim 1, further comprising:
   an environment detecting module including environment sensors, the environment sensors configured to detect an environment of the medical system; and wherein
   the control module is configured to control the movement of the base module taking into account the environment of the medical system detected by the environment sensors of the environment detecting module.

20. The medical system of claim 1, wherein the control module includes a user interface and is configured for at least one of voice control or gesture control.

21. The medical system of claim 1, wherein the medical system is configured to support and move at least one of an imaging device, medical equipment or a load.

22. A method for operating a medical system including a base module, an environment detecting module, and a control module, wherein the base module including a chassis including a plurality of rolling bodies, and adjusting devices, the plurality of rolling bodies configured to rotate about respective axes of rotation, wherein the environment detecting module includes environment sensors configured to detect an environment of the medical system, wherein the control module is configured to control movement of the base module, taking into account the environment of the medical system detected by the environment sensors of the environment detecting module, wherein the control module includes a user interface and is configured for at least one of voice control and gesture control, and wherein the method comprises:
- generating, via the control module, movement control commands as a function of diagnostic protocol of a battery management system indicative of at least one of a state-of-charge or a state-of-health of an energy store; and
- transmitting the movement control commands to the base module for execution of the movement control commands, wherein the execution of at least one of the movement control commands by the base module includes adjusting at least one of the plurality of rolling bodies in a vertical direction.

23. The method of claim 22, wherein the generating of the movement control commands includes generating the movement control commands as a function of data from a vibration sensor system, indicative of vibrations occurring during movement.

24. The method of claim 22, wherein the generating of the movement control commands includes generating the movement control commands as a function of data from an acceleration sensor system, indicative of accelerations occurring during movement.

25. The method of claim 22, wherein the generating of the movement control commands includes generating the movement control commands as a function of qualified environment data, indicative of environment of the medical system.

26. A medical system, to cover distances autonomously or semi-autonomously, the medical system comprising:
- a base structure including a chassis, the chassis including:
  - a plurality of rolling bodies, mounted to rotate about respective axes of rotation, and
  - adjusting devices, configured to rotate respective rolling bodies of the plurality of rolling bodies, the adjusting devices being adjustable in a vertical direction such that each respective rolling body, of the plurality of rolling bodies, is movable between a first position, in which the respective rolling body is in contact with a floor area, and a second position, in which the respective rolling body is spaced apart from the floor area;
- an energy storage configured to supply the medical system with energy; and
- a controller configured to control movement of the base structure taking into account at least one of a state-of-energy or state-of-charge of the energy storage.

* * * * *